United States Patent
Arai et al.

(10) Patent No.: US 11,350,904 B2
(45) Date of Patent: Jun. 7, 2022

(54) RADIOGRAPHIC IMAGING APPARATUS

(71) Applicant: FUJIFILM Corporation, Tokyo (JP)

(72) Inventors: Takahisa Arai, Kanagawa (JP);
Takeyasu Kobayashi, Kanagawa (JP);
Shunsuke Kodaira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/790,651

(22) Filed: Feb. 13, 2020

(65) Prior Publication Data

US 2020/0265571 A1     Aug. 20, 2020

(30) Foreign Application Priority Data

Feb. 14, 2019    (JP) .............................. JP2019-024729

(51) Int. Cl.
    *A61B 6/00*         (2006.01)
    *G06T 5/50*         (2006.01)
    (Continued)

(52) U.S. Cl.
    CPC ............ *A61B 6/545* (2013.01); *A61B 6/4291* (2013.01); *A61B 6/486* (2013.01); *A61B 6/502* (2013.01); *A61B 6/5235* (2013.01); *A61B 6/5241* (2013.01); *A61B 6/5264* (2013.01); *A61B 6/5294* (2013.01); *A61B 6/541* (2013.01);
    (Continued)

(58) Field of Classification Search
None
See application file for complete search history.

(56) References Cited

U.S. PATENT DOCUMENTS 7,340,034 B2     3/2008    Hayashida et al.
8,570,386 B2 *   10/2013   Castorina ................ G06T 5/003
                                                     348/208.99
(Continued)

FOREIGN PATENT DOCUMENTS

DE     102015205270 A1 *   9/2016         A61B 6/5258
JP       H0956707            3/1997
(Continued)

OTHER PUBLICATIONS

"Search Report of Europe Counterpart Application", dated Jul. 10, 2020, p. 1-p. 8.

(Continued)

*Primary Examiner* — Thomas R Artman
(74) *Attorney, Agent, or Firm* — JCIPRNET (57) ABSTRACT

A mammography apparatus (radiographic imaging apparatus) includes: a total irradiation time acquisition unit that acquires the total irradiation time of X-rays (radiation); a divided irradiation time calculation unit that calculates a divided irradiation time by dividing the total irradiation time; an imaging controller that obtains a plurality of time-division images by time-division imaging in which radiographic imaging is performed multiple times according to the divided irradiation time; a feature point recognition unit that recognizes feature points for each of the time-division images; a time-division image selection unit that selects some or all of the time-division images from the plurality of time-division images using the feature points; and a composite image generation unit that generates a composite image using the selected time-division images.

15 Claims, 5 Drawing Sheets

(51) Int. Cl.
  *G06T 7/73* (2017.01)
  *G06T 5/00* (2006.01)
  *G06V 10/10* (2022.01)
(52) U.S. Cl.
  CPC ............ *G06T 5/003* (2013.01); *G06T 5/50* (2013.01); *G06T 7/74* (2017.01); *G06V 10/10* (2022.01); *G06T 2207/10124* (2013.01); *G06T 2207/20201* (2013.01); *G06T 2207/20212* (2013.01); *G06T 2207/30068* (2013.01); *G06V 2201/03* (2022.01)

(56) References Cited

U.S. PATENT DOCUMENTS

| | | | |
|---|---|---|---|
| 8,588,551 B2 * | 11/2013 | Joshi | G06T 5/003 |
| | | | 382/294 |
| 9,076,565 B2 | 7/2015 | Shiraki et al. | |
| 9,536,336 B2 | 1/2017 | Shiraki et al. | |
| 9,782,137 B2 * | 10/2017 | Tajima | A61B 6/542 |
| 10,070,843 B2 * | 9/2018 | Kamiya | A61B 6/0487 |
| 10,163,211 B2 * | 12/2018 | Vaillant | A61B 6/5264 |
| 10,881,374 B2 * | 1/2021 | Aspelund | A61B 6/582 |
| 10,891,763 B2 * | 1/2021 | Hoornaert | G06T 7/38 |
| 2007/0071171 A1 * | 3/2007 | Hayashida | A61B 6/00 |
| | | | 378/98 |
| 2010/0165122 A1 * | 7/2010 | Castorina | H04N 5/23248 |
| | | | 348/208.4 |
| 2011/0211758 A1 * | 9/2011 | Joshi | G06T 5/002 |
| | | | 382/167 |
| 2014/0140484 A1 * | 5/2014 | Shiraki | G21K 1/025 |
| | | | 378/98 |
| 2015/0257245 A1 | 9/2015 | Tajima | |
| 2017/0000451 A1 | 1/2017 | Aspelund et al. | |
| 2017/0086773 A1 | 3/2017 | Kamiya | |
| 2017/0213343 A1 * | 7/2017 | Vaillant | A61B 6/487 |
| 2018/0247437 A1 * | 8/2018 | Hoornaert | A61B 6/504 |
| 2019/0378243 A1 * | 12/2019 | Takagi | G16H 50/20 |
| 2020/0265571 A1 * | 8/2020 | Arai | A61B 6/545 |

FOREIGN PATENT DOCUMENTS

| | | |
|---|---|---|
| JP | H0956707 A * | 3/1997 |
| JP | 2007082907 | 4/2007 |
| JP | 2014113444 | 6/2014 |
| JP | 2017064185 | 4/2017 |
| JP | 2017093646 | 6/2017 |

OTHER PUBLICATIONS

"Office Action of Japan Counterpart Application", dated Jan. 5, 2022, with English translation thereof, p. 1-p. 10.

* cited by examiner

RADIOGRAPHIC IMAGING APPARATUS

CROSS-REFERENCE TO RELATED APPLICATIONS

This application claims priority under 35 U.S.C § 119(a) to Japanese Patent Application No. 2019-024729 filed on 14 Feb. 2019. The above application is hereby expressly incorporated by reference, in its entirety, into the present application.

BACKGROUND OF THE INVENTION

1. Field of the Invention

The present invention relates to a radiographic imaging apparatus for imaging a subject using radiation.

2. Description of the Related Art

In the medical field, radiographic imaging apparatuses, such as a mammography apparatus for imaging a subject using radiation, such as X-rays, have been widely used. A radiographic imaging apparatus usually acquires one radiographic image by one-time irradiation. In addition, there is a case where a radiographic image used for diagnosis is obtained by imaging a subject multiple times from the same angle or different angles and combining or reconstructing a plurality of radiographic images obtained as a result (JP2017-064185A, corresponding to US2017/086773A1).

SUMMARY OF THE INVENTION

In a case where a radiographic image for diagnosis is obtained by combining a plurality of images obtained by imaging the subject multiple times, there is a problem in that "blurring" occurs in a generated radiographic image for diagnosis and this makes interpretation difficult in a case where there is movement of the subject during the multiple imaging operations. In a case where re-imaging is required as a result, there is also a problem that the subject is subjected to excessive exposure.

It is an object of the invention to provide a radiographic imaging apparatus that generates a radiographic image with a small amount of "blurring" even though there is movement (body movement or the like) of the subject during the multiple imaging operations in a case where a radiographic image for diagnosis is obtained by combining a plurality of images obtained by imaging the subject multiple times.

A radiographic imaging apparatus of the invention comprises: a total irradiation time acquisition unit that acquires a total irradiation time of radiation emitted to a subject in order to obtain one radiographic image; a divided irradiation time calculation unit that calculates a divided irradiation time, which is an irradiation time of radiation per imaging, by dividing the total irradiation time; an imaging controller that obtains a plurality of time-division images by time-division imaging in which radiographic imaging is performed multiple times according to the divided irradiation time; a feature point recognition unit that recognizes feature points for each of the time-division images; a time-division image selection unit that selects some or all of the time-division images from the plurality of time-division images using the feature points; and a composite image generation unit that generates a composite image using the selected time-division images.

It is preferable that the time-division image selection unit selects the time-division images, in which an amount of deviation of each of the feature points is equal to or less than a threshold value, from the plurality of captured time-division images.

It is preferable that the time-division image selection unit calculates an average position of the feature points and selects the time-division images in which an amount of deviation from the average position of the feature points is equal to or less than a threshold value.

It is preferable that, by calculating an amount of deviation of each of the feature points of the other time-division images with the feature point of a specific time-division image among the time-division images as a reference, the time-division image selection unit selects the specific time-division image and the time-division image in which the amount of deviation of the feature point is equal to or less than the threshold value.

It is preferable that the time-division image selection unit uses the feature point of the time-division image captured first, among the plurality of captured time-division images, as a reference.

It is preferable that the feature point recognition unit sequentially recognizes the feature points of the time-division images each time the time-division image is captured and the time-division image selection unit determines selection or non-selection of the time-division image each time the time-division image is captured.

It is preferable that the imaging controller continues time-division imaging until the number of time-division images selected by the time-division image selection unit reaches a specific number.

It is preferable that, in a case where the total number of captured time-division images including the time-division image not selected by the time-division image selection unit reaches the upper limit number of captured images, the imaging controller ends the time-division imaging even in a case where the number of time-division images selected by the time-division image selection unit does not reach the specific number.

It is preferable to further comprise a feature point position acquisition unit that acquires a position of the feature point appearing in each of the time-division images. It is preferable that the time-division image selection unit selects the time-division image in which an amount of deviation from the position of the feature point acquired by the feature point position acquisition unit is equal to or greater than a threshold value.

It is preferable that the feature point position acquisition unit acquires the position of the feature point from a radiographic image captured in advance.

It is preferable that the time-division image selection unit sequentially determines selection or non-selection of the time-division images by determining whether or not a position and/or a shape of each of the feature points are correctable.

It is preferable that the imaging controller stops time-division imaging in a case where the time-division image in which the position and/or the shape of each of the feature points are not correctable is generated.

It is preferable that the composite image generation unit generates the composite image by superimposition processing for superimposing the selected time-division images.

Another radiographic imaging apparatus of the invention comprises: a total irradiation time acquisition unit that acquires a total irradiation time of radiation emitted to a subject in order to obtain one radiographic image; an imaging controller that obtains a plurality of time-division images by time-division imaging in which radiographic imaging is performed multiple times according to a divided irradiation time obtained by dividing the total irradiation time into times during which no body movement of the subject occurs; and a composite image generation unit that generates a composite image using the time-division images.

It is preferable that the divided irradiation time is equal to or shorter than 150 ms.

It is preferable that, in a case where a grid is used for the time-division imaging, the divided irradiation time is set to a time during which at least a contrast of an image of the subject is higher than a contrast of an image of the grid in the time-division image.

It is preferable that the divided irradiation time is equal to or longer than 50 ms.

According to the radiographic imaging apparatus of the invention, in a case where a radiographic image for diagnosis is obtained by combining a plurality of images obtained by imaging the subject multiple times, it is possible to generate a radiographic image with a small amount of "blurring" even though there is movement of the subject during the multiple imaging operations. Since a doctor can perform interpretation using a radiographic image with a small amount of "blurring", it is possible to suppress excessive exposure for the subject by avoiding a situation in which re-imaging should be performed.

DESCRIPTION OF THE PREFERRED EMBODIMENTS

First Embodiment

Figure 1:
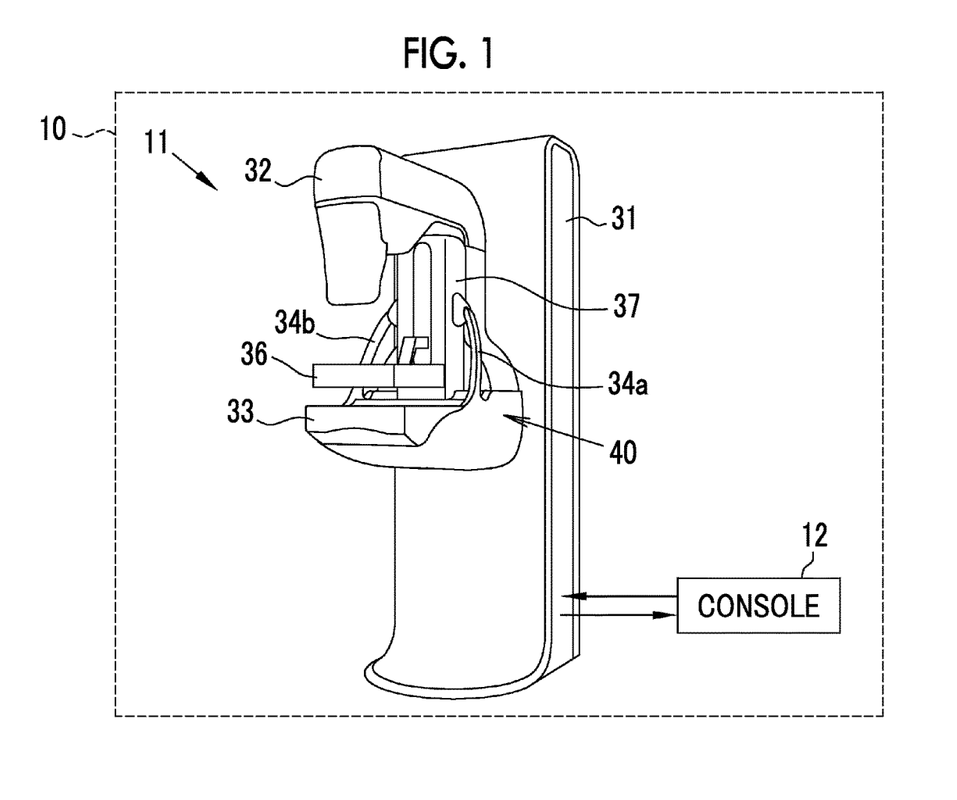
FIG. 1 is an explanatory diagram showing the configuration of a mammography apparatus.

As shown in FIG. 1, a mammography apparatus 10 that is an example of a radiographic imaging apparatus comprises an apparatus main body 11 that images the breast (hereinafter, referred to as a subject) of a subject using X-rays that are radiation and a console 12 that controls the apparatus main body 11.

The apparatus main body 11 comprises a support 31, an X-ray generation unit 32, an imaging table 33 in which an X-ray imaging unit is provided, a compression plate 36, an elevating unit 37, and the like. The X-ray generation unit 32 and the imaging table 33 are integrated to form a movable unit 40 that performs position adjustment according to the subject in the apparatus main body 11.

The imaging table 33 is a stage on which the breast that is a subject is placed, and the breast is interposed between the imaging table 33 and the compression plate 36 at the time of imaging. The X-ray imaging unit (not shown) provided in the imaging table 33 includes, for example, a flat panel detector (FPD) for imaging the subject using radiation and a grid for removing scattered radiation (static type Lysholm-Blende or mobile type Bucky-Blende). The mammography apparatus 10 has a plurality of types of grids that can be exchanged according to imaging conditions, and can also perform imaging without using a grid. In addition, a gripping unit 34a that the subject grips with the right hand and a gripping unit 34b that the subject grips with the left hand are attached to the imaging table 33. The gripping unit 34a and the gripping unit 34b are so-called armrests.

The compression plate 36 compresses the breast of the subject placed on the imaging table 33 to make the breast flat. This is to reduce the overlap of normal mammary glands so that it becomes easy to find lesion candidates, such as calcifications. The elevating unit 37 moves the compression plate 36 up and down with respect to the imaging table 33. In this manner, the elevating unit 37 supports the compression plate 36 almost in parallel to the imaging table 33 and at a specific distance according to the thickness of the breast.

The movable unit 40 can freely rotate within a predetermined angle range while maintaining the relative position and direction of the X-ray generation unit 32 and the imaging table 33. Therefore, the apparatus main body 11 can perform imaging in a state in which the imaging table 33 is horizontally disposed or the imaging table 33 is disposed so as to be inclined from the horizontal plane. Specifically, the apparatus main body 11 can perform craniocaudal imaging (CC imaging) for imaging the breast from the head-to-tail direction by arranging the imaging table 33 in the horizontal direction. The apparatus main body 11 can perform mediolateral oblique imaging (MLO imaging) for imaging the breast from the internal and external oblique directions by arranging the imaging table 33 so as to be inclined.

The X-ray generation unit 32 of the movable unit 40 can freely rotate within a predetermined range while fixing the positions of the imaging table 33 and the compression plate 36. Therefore, the apparatus main body 11 can perform so-called stereo imaging and tomosynthesis imaging. The stereo imaging is an imaging mode in which the breast of the subject fixed at a specific position and direction (for example, position and direction of CC imaging) is imaged from one inclined direction or a plurality of inclined directions having different inclination angles to obtain a perspective image (hereinafter, referred to as a stereo image) from the inclined direction. The tomosynthesis imaging is an imaging mode in which, for the breast of the subject fixed at a specific position and direction, a tomographic image (hereinafter, referred to as a tomosynthesis image) is obtained using images captured from a plurality of inclined directions.

Figure 2:
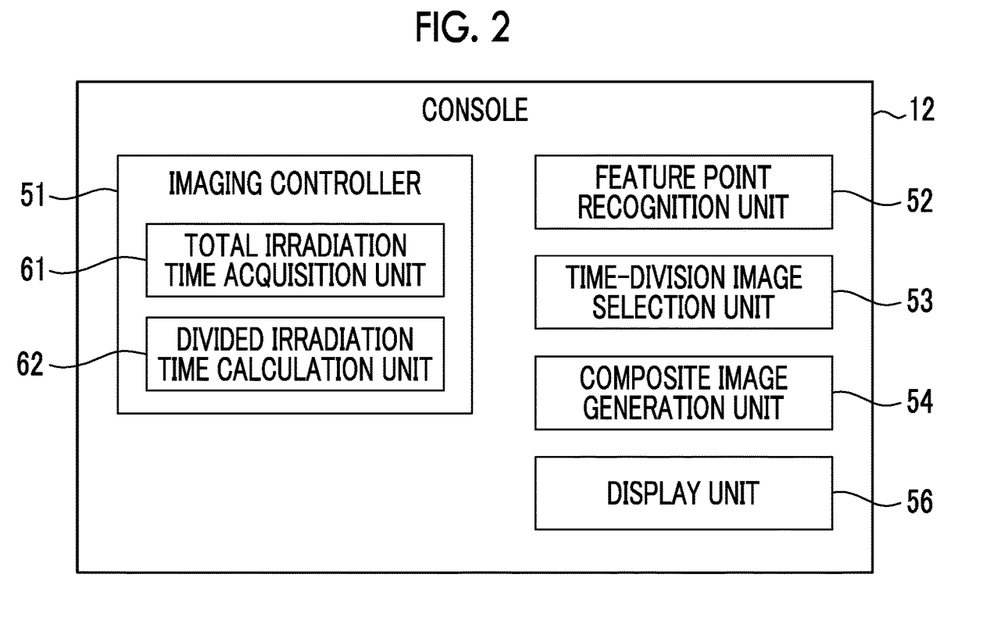
FIG. 2 is a block diagram showing the configuration of a console.

As shown in FIG. 2, the console 12 comprises an imaging controller 51, a feature point recognition unit 52, a time-division image selection unit 53, a composite image generation unit 54, and a display unit 56.

The imaging controller 51 controls the X-ray generation unit 32, the X-ray imaging unit in which the imaging table 33 is provided, and the like to perform imaging, and acquires a mammography image (radiographic image). In the present embodiment, the imaging controller 51 acquires imaging conditions, such as X-ray quality, dose, and irradiation time of X-rays emitted to the subject, by an input of a doctor or a radiology technician or by an auto exposure control (AEC) function. Then, in normal imaging, the imaging controller 51 acquires one mammography image (hereinafter, referred to as a diagnostic image) used for diagnosis and the like by performing imaging according to the acquired imaging conditions.

On the other hand, the mammography apparatus 10 has a time-division imaging function in addition to the normal imaging function described above. The time-division imaging function is a function of performing imaging multiple times in the case of acquiring a diagnostic image and combining some or all of images obtained by the multiple imaging operations (hereinafter, referred to as time-division images) to obtain one diagnostic image. That is, in the case of performing time-division imaging, the imaging controller 51 performs imaging (radiographic imaging) multiple times according to a predetermined "divided irradiation time", thereby obtaining a plurality of time-division images 91 (refer to FIG. 4). In addition, each time-division imaging is performed at the same angle. Imaging at the same angle refers to imaging with the positions of the X-ray generation unit 32, the X-ray imaging unit provided in the imaging table 33, and the like fixed with respect to the subject. This is because one diagnostic image is obtained by superimposing and combining images obtained by time-division imaging.

For the time-division imaging, the imaging controller 51 comprises a total irradiation time acquisition unit 61 and a divided irradiation time calculation unit 62.

In the case of performing time-division imaging, the total irradiation time acquisition unit 61 acquires the irradiation time (hereinafter, referred to as total irradiation time) of X-rays emitted to the subject in order to obtain one diagnostic image. The total irradiation time is included in the imaging conditions, or can be set using the imaging conditions. Therefore, the total irradiation time acquisition unit 61 acquires the total irradiation time by acquiring the imaging conditions.

In the case of performing time-division imaging, the divided irradiation time calculation unit 62 determines the number of times of time-division imaging (hereinafter, referred to as the number of divisions), and calculates a divided irradiation time using the total irradiation time. In a case where there is an explicit setting, the number of times of time-division imaging is determined according to the setting. In a case where there is no explicit setting, the number of times of time-division imaging is automatically determined based on the imaging conditions and the like. The divided irradiation time is an X-ray irradiation time per imaging in time-division imaging.

In the present embodiment, the divided irradiation time is calculated by evenly dividing the total irradiation time using the number of times of time-division imaging. For example, in a case where the total irradiation time is "T" (seconds) and the number of times of time-division imaging is "N" (times), the divided irradiation time is T/N (seconds). The divided irradiation time calculation unit 62 can divide the total irradiation time unevenly. For example, assuming that the total irradiation time is "T" (seconds), the number of times of time-division imaging is "N" (times), and the divided irradiation time in each time-division imaging is $\tau_N$ (seconds), the value of $T_N$ can be individually determined under the constraint satisfying $T=\Sigma\tau_N$. For example, the divided irradiation time $\tau_2$ of the second time-division imaging can be set to be longer than the divided irradiation time $\tau_1$ of the first time-division imaging ($\tau_1<\tau_2$).

In the case of performing imaging using a stationary grid (Lysholm-Blende), the divided irradiation time calculation unit 62 determines the number of divisions to such an extent that the grid image (so-called "Lys eye") is not a problem, and calculates the divided irradiation time in each imaging.

Figure 4:
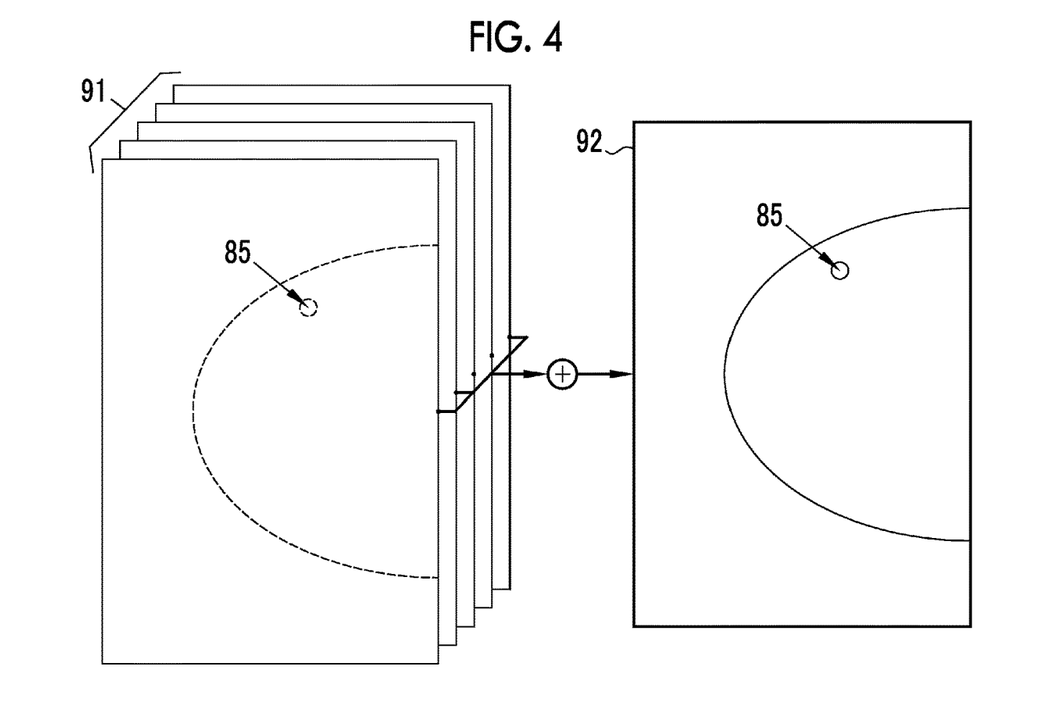
FIG. 4 is an explanatory diagram showing time-division images and a composite image.

The "extent that the Lys eye is not a problem" refers to a range in the time-division image 91 in which at least the contrast of the image of the subject falls within a range higher than the contrast of the grid image. It is preferable to set the number of divisions and the divided irradiation time so as to be small to such an extent that the Lys eye can be substantially neglected, that is, such an extent that the contrast of the grid image with respect to the contrast of the image of the subject in the time-division image 91 can be substantially neglected. Although depending on specific imaging conditions, typically, in the case of performing time-division imaging using a stationary grid, the number of divisions is, for example, about "15" and the divided irradiation time is 100 ms (milliseconds).

It is preferable to set the number of divisions and the divided irradiation time within a range in which no body movement occurs. That is, the number of divisions is set to a number for which no body movement occurs. That is, the divided irradiation time is set to a time during which no body movement occurs. "No body movement occurs" means that defects, such as image blurring caused by the body movement of the subject (movement of the subject), in the time-division image 91 are so small as to be substantially neglected.

Specifically, the number of divisions is preferably "5" or more and "25" or less, and particularly preferably "10" or more and "20" or less. This is because, in a case where the number of divisions is less than "5", the number of divisions is so small that it is difficult to set the divided irradiation time to a time during which no body movement of the subject occurs, and as a result, it is difficult to obtain the effect of time-division imaging. In addition, this is because, in a case where the number of divisions is larger than "25", only the number of times of imaging is so large that the effect of time-division imaging is difficult to extend. In addition, as the number of divisions increases, the time-divided irradiation time decreases. As a result, a disadvantage that the Lys eye is likely to be noticeable in the time-division image 91 increases. Depending on the imaging conditions and the like, the number of divisions may not be a parameter completely independent of the divided irradiation time but may have to be set dependently depending on the divided irradiation time that can be set. In the present embodiment, the number of divisions is "15".

The divided irradiation time is preferably 50 ms or more and 150 ms or less, and particularly preferably 75 ms or more and 125 ms or less. This is because, in a case where the divided irradiation time is less than 50 ms, the divided irradiation time is so short that the Lys eye is likely to be a problem in the time-division image 91. This is because, in a case where the divided irradiation time exceeds 150 ms, the typical body movement of the subject tends to be a size that cannot be neglected in the time-division image 91. Depending on the imaging conditions, the divided irradiation time may not be a parameter completely independent of the number of divisions but may have to be set dependently depending on the number of divisions that can be set. In the present embodiment, the divided irradiation time is 100 ms.

The feature point recognition unit 52 recognizes feature points for each time-division image 91. The feature points include calcifications, tumors, mammary glands, or other tissues or structures, or a disorder in their arrangement. In the present embodiment, the feature point recognition unit 52 recognizes calcification 85 (refer to FIG. 4) as a feature point. In addition, the feature point recognition unit 52 can recognize a plurality of types of feature points, such as calcifications and mammary glands. In addition, the feature point recognition unit 52 can recognize one or a plurality of feature points. For example, in a case where there are a plurality of calcifications, one or more of these can be recognized as feature points.

The time-division image selection unit 53 selects some or all time-division images 91 from the plurality of time-division images 91 using the feature points recognized by the feature point recognition unit 52. In this manner, the time-division image selection unit 53 determines time-division images to be used by the composite image generation unit 54 to generate a composite image. In the present embodiment, the time-division image selection unit 53 selects the time-division image 91, in which the amount of deviation of the recognized feature point (calcification 85) is equal to or less than a predetermined threshold value, from the plurality of captured time-division images 91. More specifically, the time-division image selection unit 53 calculates the average position of the feature points. Then, the time-division image 91 in which the calculated amount of deviation of each feature point from the average position is equal to or less than a predetermined threshold value is selected.

Instead of calculating the average position as described above, by calculating the deviation of the feature points of other time-division images 91 with a feature point (calcification 85) of the specific time-division image 91 among the time-division images 91 as a reference, the time-division image selection unit 53 can select the specific time-division image 91 and the time-division image 91 in which the amount of deviation of the feature point is equal to or less than a predetermined threshold value. That is, the time-division image selection unit 53 can select time-division images, which are to be used to generate a composite image, with the feature point of one randomly selected time-division image 91 as a reference instead of the average position of the feature points. In this case, for example, it is preferable that the time-division image selection unit 53 uses a feature point of the time-division image 91, which is captured first among the plurality of captured time-division images 91, as a reference. This is because, in many cases, the subject is likely to be stationary according to the instruction of the doctor or the radiology technician at the start of imaging but the subject often moves during the subsequent time-division imaging.

The composite image generation unit 54 generates a composite image 92 (refer to FIG. 4) using the plurality of time-division images 91 selected by the time-division image selection unit 53. In the present embodiment, the composite image generation unit 54 generates a composite image by superimposition processing for superimposing the plurality of time-division images 91 selected by the time-division image selection unit 53. In the case of combining the time-division images 91, the composite image generation unit 54 can adjust positions, at which one or a plurality of time-division images 91 are superimposed, so that the positions of the feature points of the respective time-division images 91 match each other. This is to improve the sharpness of the composite image 92 (in particular, the sharpness of the calcification 85 that is a feature point). The correction processing on the time-division image 91 for position adjustment performed herein can include, for example, parallel movement, rotation, and/or deformation of the time-division image 91.

In the mammography apparatus 10, the composite image 92 generated by the composite image generation unit 54 is subjected to image processing or the like as necessary to obtain a diagnostic image. The composite image generation unit 54 can perform image processing required for providing the composite image 92 to a doctor or the like as a diagnostic image. For this reason, the composite image generation unit 54 also functions as a diagnostic image generation unit that generates a diagnostic image. Hereinafter, a diagnostic image in the case of performing time-division imaging is simply referred to as the composite image 92 regardless of whether or not image processing is performed in order to distinguish the diagnostic image in the case of performing time-division imaging from diagnostic images acquired by normal imaging.

The display unit 56 is a monitor of the console 12, and displays a diagnostic image. That is, in the case of performing time-division imaging, the display unit 56 displays the composite image 92. In addition, the display unit 56 can perform display relevant to the operation of the mammography apparatus 10, such as a setting menu, as necessary. In addition, the display unit 56 can display some or all of the time-division images 91.

Figure 3:
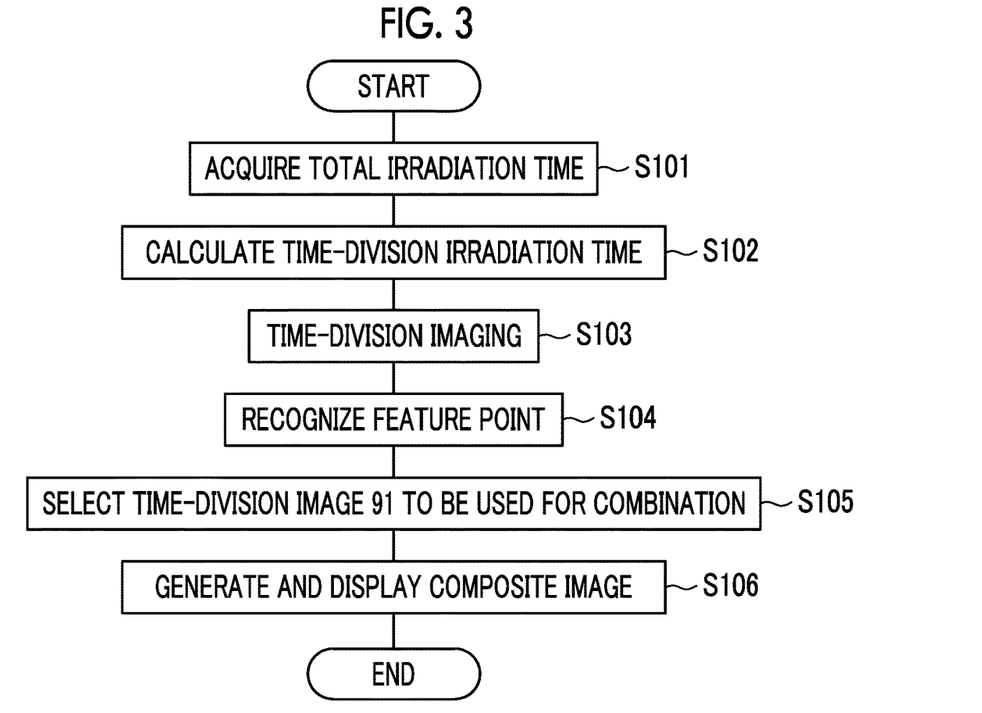
FIG. 3 is a flowchart showing steps of imaging and composite image generation.

Hereinafter, an operation in which the mammography apparatus 10 configured as described above performs time-division imaging in order to obtain the composite image 92 will be described. As shown in FIG. 3, in the case of obtaining a diagnostic image (composite image 92) by the time-division imaging function, upon receiving settings such as imaging conditions by the imaging controller 51, the total irradiation time acquisition unit 61 acquires the total irradiation time of X-rays from the imaging conditions settings and the like (step S101), and the divided irradiation time calculation unit 62 determines the number of divisions of time-division imaging and calculates the divided irradiation time (step S102).

Thereafter, in response to an imaging execution instruction from a doctor or the like, the imaging controller 51 executes time-division imaging by the determined number of divisions according to the divided irradiation time calculated by the divided irradiation time calculation unit 62 (step S103). As a result, as shown in FIG. 4, the mammography apparatus 10 obtains the time-division images 91 corresponding to the number of divisions.

In a case where the time-division images 91 are obtained as described above, the feature point recognition unit 52 recognizes the feature points of each time-division image 91 (step S104). In the present embodiment, the calcification 85 reflected in each time-division image 91 is recognized. Thereafter, the time-division image selection unit 53 selects a plurality of time-division images 91 to be used for combination, which are a combination having a small deviation in the position of the calcification 85 that is a feature point (step S105). Then, the composite image generation unit 54 generates the composite image 92 by superimposing the time-division images 91 selected by the time-division image selection unit 53 (refer to FIG. 4), and the display unit 56 displays the generated composite image 92 (step S106).

As described above, the mammography apparatus 10 performs time-division imaging multiple times in order to obtain one diagnostic image. Then, it is carefully examined whether or not each of the plurality of time-division images 91 obtained by time-division imaging is to be used for the composite image 92 using the position of the calcification 85 that is a feature point, and only the time-division image 91 suitable for generating the composite image 92 is used for combination. For this reason, in a case where there is movement of the subject during time-division imaging, the time-division image 91 captured in a case where there is movement of the subject is not used for combination. As a result, the composite image 92 becomes a diagnostic image with a small amount of "blurring". That is, in the case of obtaining one diagnostic image by time-division imaging, the mammography apparatus 10 can generate and display a diagnostic image with a small amount of "blurring" even though there is movement of the subject. As a result, even though there is movement of the subject, it is possible to suppress excessive exposure for the subject by avoiding re-imaging.

Second Embodiment

In the first embodiment described above, after performing time-division imaging by the number of divisions, the time-division image 91 to be used for combination is selected from a plurality of already obtained time-division images 91. However, the mammography apparatus 10 can determine whether or not to use the acquired time-division image 91 for combination each time time-division imaging is performed. That is, the feature point recognition unit 52 can be configured to sequentially recognize the feature points of the time-division image 91 in real time each time the time-division image 91 is captured, and the time-division image selection unit 53 can be configured to determine selection or non-selection of the time-division image 91 each time the time-division image 91 is captured.

Figure 5:
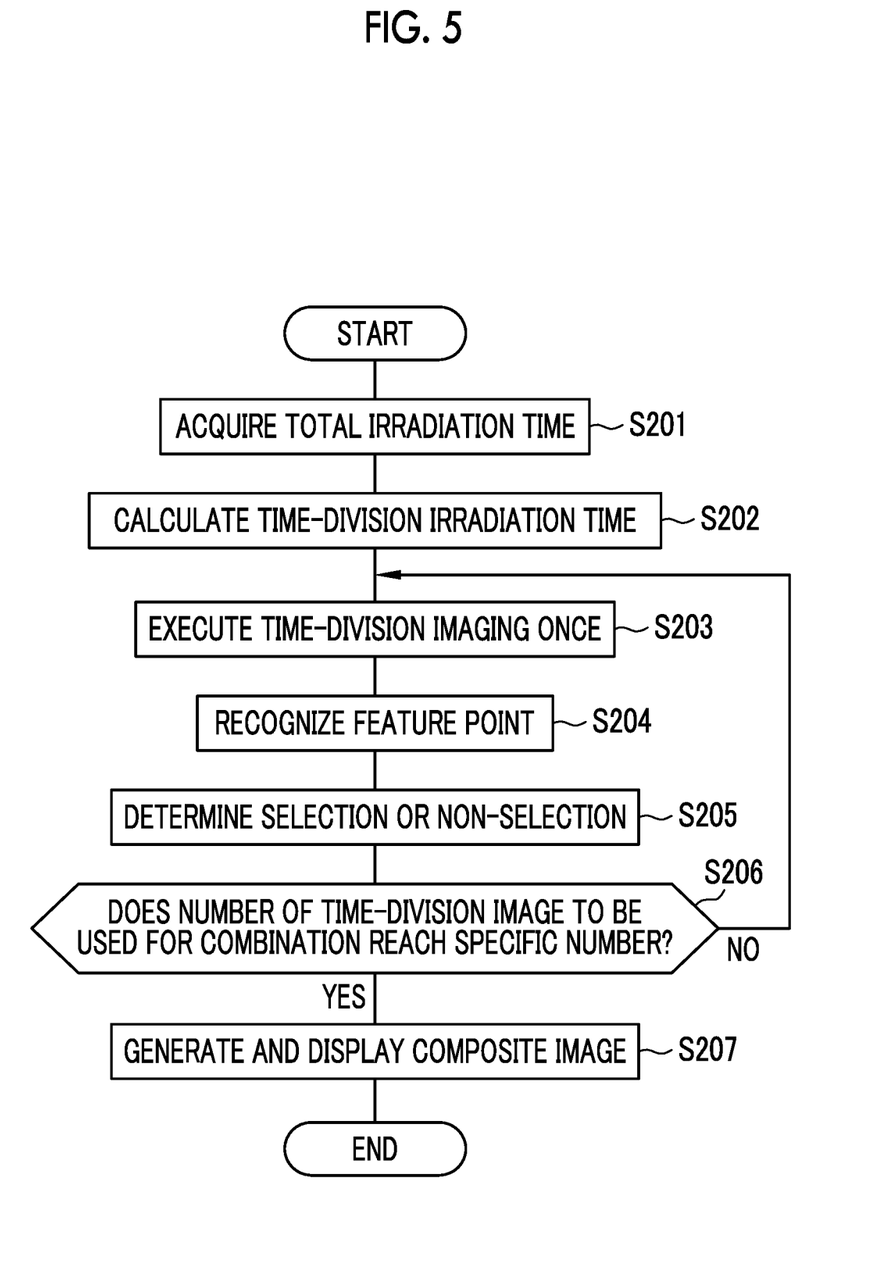
FIG. 5 is a flowchart showing steps of imaging and composite image generation in a second embodiment.

In this case, as shown in FIG. 5, the total irradiation time acquisition unit 61 acquires the total irradiation time (step S201), and the divided irradiation time calculation unit 62 determines the number of divisions and calculates the divided irradiation time (step S202). Then, in a case where a doctor or the like inputs an imaging execution instruction, the imaging controller 51 executes time-division imaging once (step S203). Then, the feature point recognition unit 52 does not wait for the completion of the subsequent time-division imaging and recognizes feature points for the time-division image 91 captured this time (step S204), and the time-division image selection unit 53 determines selection or non-selection of the time-division image 91 (step S205).

Thereafter, the imaging controller 51 continues time-division imaging until the number of time-division images 91 selected by the time-division image selection unit 53 reaches a specific number (step S206). That is, the imaging controller 51 ends the time-division imaging in a case where the number of time-division images 91 to be used for combination reaches a specific number (step S206). This is to prevent the granularity of the composite image 92 from worsening since the number of time-division images 91 used for the composite image 92 is too small. Therefore, the specific number is, for example, the number of time-division images 91 necessary for combining one diagnostic image (that is, the same number as the number of divisions). Needless to say, since any granularity that causes few problems in diagnosis is possible, the specific number can be set to a number smaller than the number of divisions.

After the end of the time-division imaging, the composite image generation unit 54 generates the composite image 92 using the time-division images 91 selected in advance by the time-division image selection unit 53 as described above, and the display unit 56 displays the generated composite image 92 (step S207).

As described above, in the case of determining whether or not to use the acquired time-division image 91 for combination each time time-division imaging is performed, the number of time-division images 91 to be captured (specific number) is determined by the quality of the composite image 92, such as the granularity of the composite image 92. For this reason, according to the mammography apparatus 10 of the second embodiment, the quality of the composite image 92 is kept constant, and it is easier to stably provide a high-quality diagnostic image than in the case of the mammography apparatus 10 of the first embodiment in which the number of time-division images 91 used for combination is reduced depending on the degree of movement of the subject.

The mammography apparatus 10 of the second embodiment preferably further has a configuration in which the total number of captured time-division images 91 is counted and an upper limit value (hereinafter, referred to as the upper limit number of captured images) is set for the total number of captured images. That is, in a case where the total number of captured time-division images 91 including the time-division image 91 not selected by the time-division image selection unit 53 reaches the upper limit number of captured images, the imaging controller 51 is preferably configured to end the imaging even in a case where the number of time-division images selected by the time-division image selection unit 53 does not reach the specific number.

Figure 6:
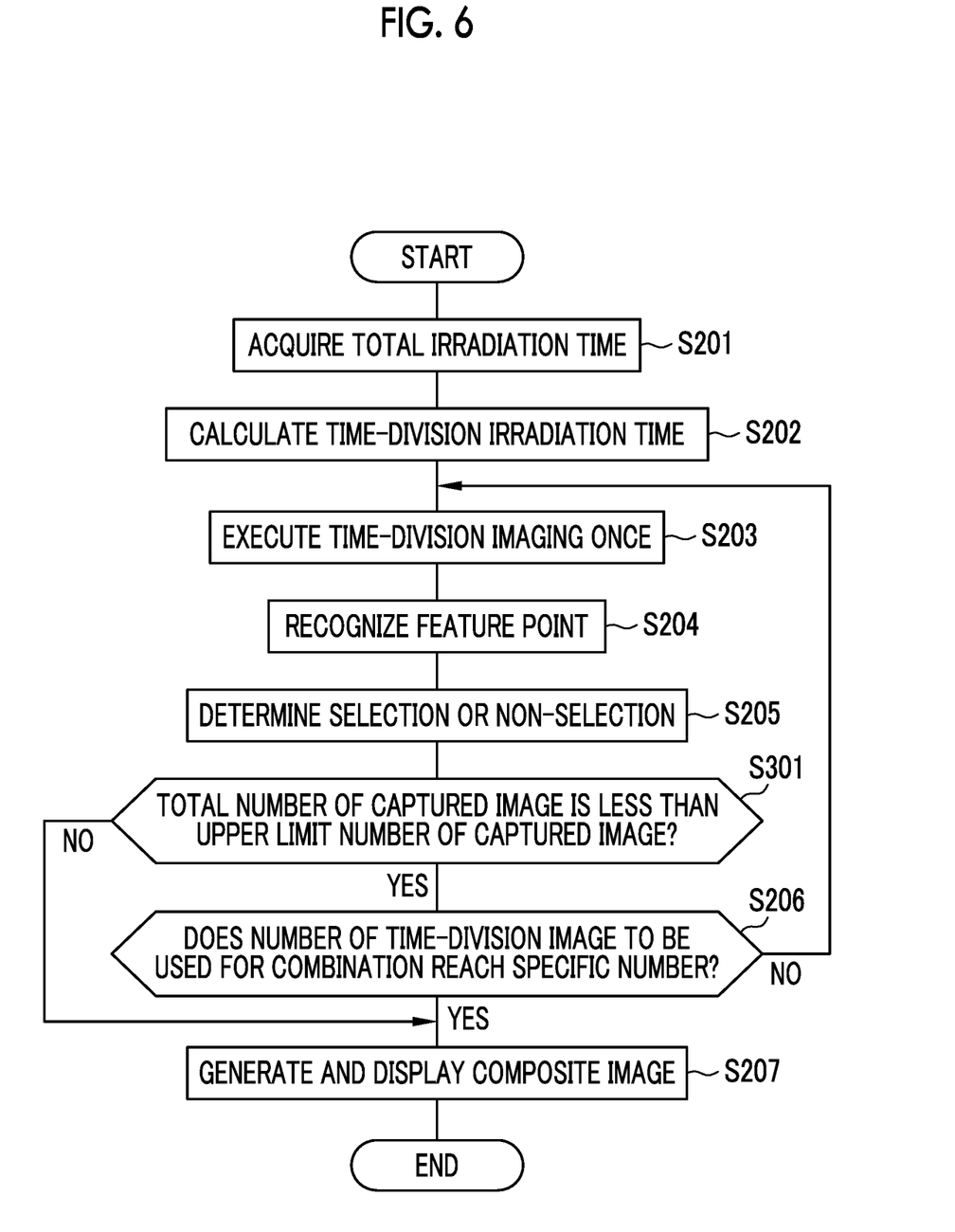
FIG. 6 is a flowchart showing steps of imaging and composite image generation in a modification example.

Specifically, as shown in FIG. 6, the imaging controller 51 compares the upper limit value of the total number of captured images with the number of actually captured time-division images 91 each time time-division imaging is captured, and the time-division imaging is forcibly ended in a case where the total number of captured images becomes equal to or greater than the upper limit number of captured images. In a case where the time-division imaging is simply continued until the specific number is reached, the amount of exposure received by the subject may become too large depending on the movement of the subject. However, by setting the upper limit number of captured images in the time-division imaging as described above, the amount of exposure can always be kept below a certain level.

Figure 7:
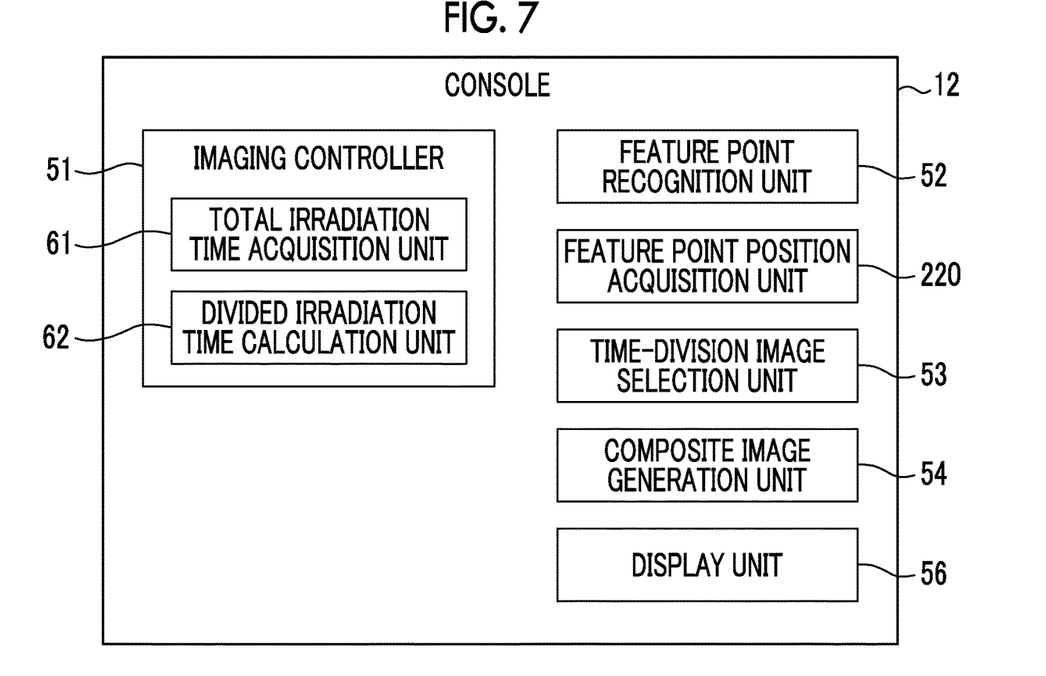
FIG. 7 is a block diagram showing the configuration of a console in a modification example.

In the second embodiment described above, as shown in FIG. 7, a feature point position acquisition unit 220 that acquires the position of the feature point appearing in the time-division image 91 is provided, and the time-division image selection unit 53 can select the time-division image 91, in which the amount of deviation from the position of the feature point acquired by the feature point position acquisition unit 220 is equal to or less than a predetermined threshold value, as the time-division image 91 to be used for combination. The feature point position acquisition unit 220 acquires the position of the feature point from a mammography image (radiographic image), such as a diagnostic image obtained by imaging the subject in advance, for example. In this manner, since selection or non-selection criteria are determined in advance, it is possible to determine selection or non-selection of the time-division image 91 each time time-division imaging is performed from the first time-division image 91. Needless to say, as in the first embodiment, selection or non-selection of the second and subsequent time-division images 91 may be determined with the feature point of the first time-division image 91 as a reference.

In the second embodiment, the time-division image selection unit 53 can sequentially determine selection or non-selection of the time-division image 91 by determining whether or not the position and/or the shape of the feature point can be corrected. The correction referred to herein is a correction to adjust positions, at which one or a plurality of time-division images 91 are superimposed, so that the positions of the feature points of the respective time-division images 91 match each other in a case where the composite image generation unit 54 combines the time-division images

91. For example, the correction referred to herein is parallel movement, rotation, and/or deformation of the time-division image 91.

In a case where the time-division image selection unit 53 sequentially determines selection or non-selection of the time-division image 91 by determining whether or not correction is possible as described above, the imaging controller 51 preferably stops time-division imaging in a case where the time-division image 91 is generated in which the position and/or the shape of the feature point cannot be corrected. This is to prevent a situation in which, since this is a case where there is large movement of the subject, the time-division image 91 that can be used for the composite image 92 is not obtained even though time-division imaging is continued thereafter, and as a result, the subject is unnecessarily exposed.

Third Embodiment

In the above-described first and second embodiments and modification examples thereof, the time-division images 91 to be used for the composite image 92 are carefully selected using feature points after setting the number of divisions and the divided irradiation time in time-division imaging within a range in which no body movement occurs. However, as long as the number of divisions and the divided irradiation time in time-division imaging are set within the range in which no body movement occurs, it is possible to omit the feature point recognition processing and the processing for selecting the time-division images 91 using the feature points and generate the composite image 92 using some or all of the time-division images 91.

Figure 8:
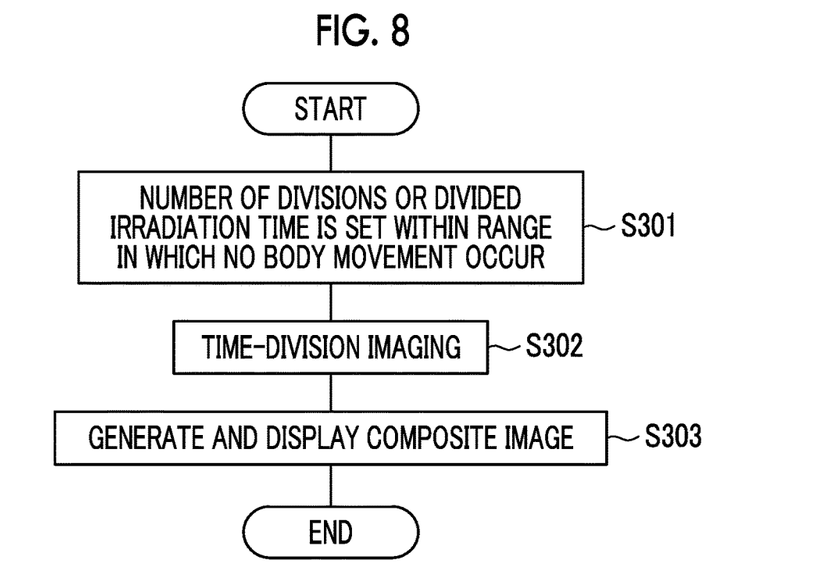
FIG. 8 is a flowchart of the third embodiment.

For example, as shown in FIG. 8, in a case where the number of divisions or the divided irradiation time is set in advance within a range in which no body movement occurs (step S301), the total irradiation time acquisition unit 61 acquires the total irradiation time of X-rays from the setting of imaging conditions and the like, and the divided irradiation time calculation unit 62 calculates the divided irradiation time for time-division imaging (a case where the number of divisions is set in step S301) or the number of divisions (case where the divided irradiation time is set in step S301) according to the set number of divisions or the set divided irradiation time. Then, in a case where a doctor or the like inputs an instruction to perform imaging, time-division imaging is automatically performed according to the setting of the number of divisions and the divided irradiation time (step S302). That is, the imaging controller 51 obtains a plurality of time-division images 91 by time-division imaging according to the divided irradiation time obtained by dividing the total irradiation time into times during which no body movement of the subject occurs. Then, the composite image generation unit 54 generates the composite image 92 by superimposing some or all of the obtained time-division images 91, and the display unit 56 displays the generated composite image 92 (step S303).

As described above, in a case where the number of divisions or the divided irradiation time is set in advance within a range in which no body movement occurs, the body movement of the subject in each time-division image 91 hardly becomes a problem. For this reason, the composite image 92 generated by the composite image generation unit 54 is a diagnostic image with a small amount of "blurring". The third embodiment is particularly useful in that setting and imaging are simple and accordingly imaging can be performed quickly and any time-division image 91 can be selected for convenience of diagnosis from a series of time-division images 91, in which body movement of the subject does not matter, so that and the composite image 92 can be freely generated and regenerated.

In the above embodiments and the like, the mammography apparatus 10 has been described as an example. However, the invention is also suitable for a radiographic imaging apparatus capable of performing time-division imaging other than the mammography apparatus 10.

In the embodiments described above, the hardware structures of processing units for executing various kinds of processing, such as the imaging controller 51, the total irradiation time acquisition unit 61, the divided irradiation time calculation unit 62, the feature point recognition unit 52, the time-division image selection unit 53, the composite image generation unit 54, and the feature point position acquisition unit 220, are various processors shown below. The various processors include a central processing unit (CPU) that is a general-purpose processor that executes software (program) to function as various processing units, a programmable logic device (PLD) that is a processor whose circuit configuration can be changed after manufacture, such as a graphical processing unit (GPU) and a field programmable gate array (FPGA), and a dedicated electric circuit that is a processor having a circuit configuration that is designed for exclusive use in order to execute various kinds of processing.

One processing unit may be configured by one of various processors, or may be a combination of two or more processors of the same type or different types (for example, a combination of a plurality of FPGAs, a combination of a CPU and an FPGA, or a combination of a CPU and a GPU). Alternatively, a plurality of processing units may be configured by one processor. As an example of configuring a plurality of processing units using one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: mammography apparatus
11: apparatus main body
12: console
31: support
32: X-ray generation unit
33: imaging table
34*a*: gripping unit
34*b*: gripping unit
36: compression plate
37: elevating unit
40: movable unit
51: imaging controller
52: feature point recognition unit
53: time-division image selection unit
54: composite image generation unit
56: display unit 85: calcification
61: total irradiation time acquisition unit
62: divided irradiation time calculation unit
91: time-division image
92: composite image
220: feature point position acquisition unit
S101 to S303: operation step

What is claimed is:

1. A radiographic imaging apparatus, comprising:
a processor configured to:
perform a total irradiation time acquisition that acquires a total irradiation time of radiation emitted to a subject in order to obtain one radiographic image;
perform a divided irradiation time calculation that calculates a divided irradiation time, which is an irradiation time of radiation per imaging, by dividing the total irradiation time;
perform an imaging control that obtains a plurality of time-division images by time-division imaging in which radiographic imaging is performed multiple times according to the divided irradiation time, wherein the divided irradiation time ranges between 50 ms and 150 ms;
perform a feature point recognition that recognizes feature points for each of the time-division images;
perform a time-division image selection that selects some or all of the time-division images from the plurality of time-division images using the feature points; and
perform a composite image generation that generates a composite image using the selected time-division images.

2. The radiographic imaging apparatus according to claim 1,
wherein in the time-division image selection, the processor selects the time-division images, in which an amount of deviation of each of the feature points is equal to or less than a threshold value, from the plurality of captured time-division images.

3. The radiographic imaging apparatus according to claim 2,
wherein in the time-division image selection, the processor calculates an average position of the feature points and selects the time-division images in which an amount of deviation from the average position of the feature points is equal to or less than a threshold value.

4. The radiographic imaging apparatus according to claim 2,
wherein, in the time-division image selection, by calculating an amount of deviation of each of the feature points of the other time-division images with the feature point of a specific time-division image among the time-division images as a reference, the processor selects the specific time-division image and the time-division image in which the amount of deviation of the feature point is equal to or less than the threshold value.

5. The radiographic imaging apparatus according to claim 4,
wherein in the time-division image selection, the processor uses the feature point of the time-division image captured first, among the plurality of captured time-division images, as a reference.

6. The radiographic imaging apparatus according to claim 1,
wherein in the feature point recognition, the processor sequentially recognizes the feature points of the time-division images each time the time-division image is captured, and in the time-division image selection, the processor determines selection or non-selection of the time-division image each time the time-division image is captured.

7. The radiographic imaging apparatus according to claim 6,
wherein in the imaging control, the processor continues time-division imaging until the number of time-division images selected by the time-division image selection unit reaches a specific number.

8. The radiographic imaging apparatus according to claim 7,
wherein, in a case where the total number of captured time-division images including the time-division image not selected by the processor in the time-division image selection reaches the upper limit number of captured images, the processor in the imaging control ends the time-division imaging even in a case where the number of time-division images selected by the processor in the time-division image selection does not reach the specific number.

9. The radiographic imaging apparatus according to claim 6, the processor further configured to:
perform a feature point position acquisition that acquires a position of the feature point appearing in each of the time-division images,
wherein in the time-division image selection, the processor selects the time-division image in which an amount of deviation from the position of the feature point acquired by the processor in the feature point position acquisition is equal to or greater than a threshold value.

10. The radiographic imaging apparatus according to claim 9,
wherein in the feature point position acquisition, the processor acquires the position of the feature point from a radiographic image captured in advance.

11. The radiographic imaging apparatus according to claim 6,
wherein in the time-division image selection, the processor sequentially determines selection or non-selection of the time-division images by determining whether or not a position and/or a shape of each of the feature points are correctable.

12. The radiographic imaging apparatus according to claim 11,
wherein in the imaging control, the processor stops time-division imaging in a case where the time-division image in which the position and/or the shape of each of the feature points are not correctable is generated.

13. The radiographic imaging apparatus according to claim 1,
wherein in the composite image generation, the processor generates the composite image by superimposition processing for superimposing the selected time-division images.

14. A radiographic imaging apparatus, comprising:
a processor configured to:
perform a total irradiation time acquisition that acquires a total irradiation time of radiation emitted to a subject in order to obtain one radiographic image;
perform a divided irradiation time calculation that calculates a divided irradiation time, which is an irradiation time of radiation per imaging, by dividing the total irradiation time;
perform an imaging control that obtains a plurality of time-division images by time-division imaging in which radiographic imaging is performed multiple times according to the divided irradiation time;
perform a feature point recognition that recognizes feature points for each of the time-division images;
perform a time-division image selection that selects some or all of the time-division images from the plurality of time-division images using the feature points; and
perform a composite image generation that generates a composite image using the selected time-division images,
wherein in the time-division image selection, the processor selects the time-division images, in which an amount of deviation of each of the feature points is equal to or less than a threshold value, from the plurality of captured time-division images, and the processor calculates an average position of the feature points and selects the time-division images in which an amount of deviation from the average position of the feature points is equal to or less than a threshold value.

15. A radiographic imaging apparatus, comprising:
a processor configured to:
   perform a total irradiation time acquisition that acquires a total irradiation time of radiation emitted to a subject in order to obtain one radiographic image;
   perform a divided irradiation time calculation that calculates a divided irradiation time, which is an irradiation time of radiation per imaging, by dividing the total irradiation time;
   perform an imaging control that obtains a plurality of time-division images by time-division imaging in which radiographic imaging is performed multiple times according to the divided irradiation time;
   perform a feature point recognition that recognizes feature points for each of the time-division images;
   perform a time-division image selection that selects some or all of the time-division images from the plurality of time-division images using the feature points; and
   perform a composite image generation that generates a composite image using the selected time-division images,
wherein in the feature point recognition, the processor sequentially recognizes the feature points of the time-division images each time the time-division image is captured, and in the time-division image selection, the processor determines selection or non-selection of the time-division image each time the time-division image is captured.

* * * * *